United States Patent [19]

Vorbrueggen

[11] Patent Number: 5,093,490

[45] Date of Patent: Mar. 3, 1992

[54] PROCESS FOR OPTICAL RESOLUTION OF BICYCLO[3.3.0]OCTANE-3,7-DIONE-2 CARBOXYLIC ACID ESTERS AND THEIR 7-MONOKETALS

[75] Inventor: Helmut Vorbrueggen, Berlin, Fed. Rep. of Germany

[73] Assignee: Schering Aktiengesellschaft, Berlin and Bergkamen

[21] Appl. No.: 449,838

[22] PCT Filed: Mar. 11, 1988

[86] PCT No.: PCT/DE88/00149

§ 371 Date: Nov. 13, 1989

§ 102(e) Date: Nov. 13, 1989

[87] PCT Pub. No.: WO88/07050

PCT Pub. Date: Sep. 22, 1988

[30] Foreign Application Priority Data

Mar. 13, 1987 [DE] Fed. Rep. of Germany ....... 3708536

[51] Int. Cl.$^5$ .......................... C07J 1/00; C07J 75/00; C07C 405/00; C07C 177/00
[52] U.S. Cl. .......................... 540/31; 540/32; 540/116; 552/625; 552/641; 549/341; 549/345; 560/119; 560/217
[58] Field of Search .............. 552/625, 641; 540/32, 540/31, 116; 549/341, 345; 560/119, 217

[56] References Cited

U.S. PATENT DOCUMENTS 2,154,272  4/1939  Hildebrandt et al. ............. 552/625
4,912,251  3/1990  Skuballa ........................... 560/119

FOREIGN PATENT DOCUMENTS

88/05429  7/1988  World Int. Prop. O. ............ 560/119

Primary Examiner—Mukund J. Shah
Assistant Examiner—E. L. Ward
Attorney, Agent, or Firm—Millen, White & Zelano

[57] ABSTRACT

The invention relates to a process for the production of (+)-bicyclo[3.3.0]octan-3-one-2 carboxylic acid steroid esters of formula I in which
X means oxygen or the radicals $-O-(CH_2)_n-O-$ or $-O-CH_2-C(CH_3)_2-CH_2-O-$,
n means 2 or 3
$R_2$ means hydrogen or methyl,
Y means the radicals X or $X_1$,
$X_1$ means the radicals $OCH_3$ or $OCOR_3$,
$R_3$ means methyl, ethyl, phenyl, benzyl or pivalyl and the radical the radicals -continued

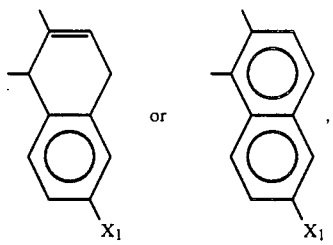

and X and $X_1$ have the meanings indicated above, characterized in that D,L-bicyclo[3.3.0]octan-3-one-2 carboxylic acid esters of formula II

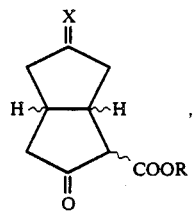  (II)

in which
X has the meaning indicated above and R is an alkyl group with 1-4 carbon atoms, with optically active steroids with a free 17'beta hydroxy group of formula III

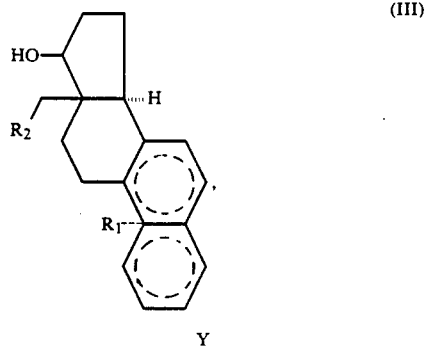  (III)

in which $R_2$ and the radical

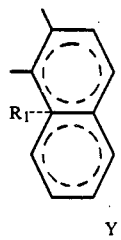

have the meanings indicated above, in the presence of a nucleophilic or acid catalyst is converted into the diastereomeric steroid esters and the optically pure steroid esters of formula I are obtained as crystallizates.

10 Claims, No Drawings

PROCESS FOR OPTICAL RESOLUTION OF BICYCLO[3.3.0]OCTANE-3,7-DIONE-2 CARBOXYLIC ACID ESTERS AND THEIR 7-MONOKETALS

DESCRIPTION

The invention relates to a process for the production of (+)-bicyclo[3.3.0]octan-3-one-2 carboxylic acid steroid esters.

Bicyclo[3.3.0]octane-3,7-dione-2 carboxylic acid esters represent important intermediate products for the production of carbacyclin derivatives and sesquiterpenes and can easily be produced according to a new process (German patent application P 3702385.3).

It has now been found that in the transesterification of these bicyclo[3.3.0]octane-3,7-dione-2 carboxylic acid esters with naturally configured steroids, which contain a free 17beta hydroxyl group, surprisingly only the derivatives with the absolute configuration represented in formula I crystallize out, while the corresponding diastereomeric esters IV remain in solution and can be recovered from the mother liquors in high optical yields.

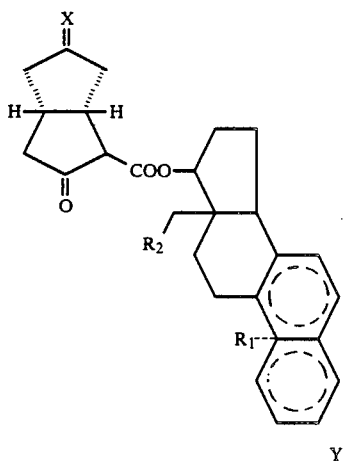
(I)

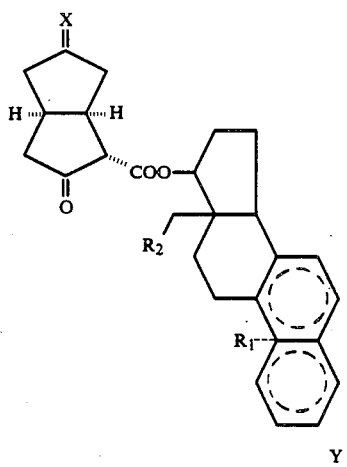
(IV)

The object of the invention is thus the optical resolution of the racemic D,L-bicyclo[3.3.0]octane-3,7-dione carboxylic acid ester derivatives II by transesterification with steroids with a free 17beta hydroxyl group, especially with aromatic A ring, of formula III and subsequent crystallization to steroid esters, and only the enantiomers, with the absolute configuration indicated in general formula I, crystallize out in a nearly optically pure manner, while steroid esters IV, diastereomeric to I, can be recovered in optical yields of about 90% from the mother liquor.

Thus the invention relates to a process for the production of (+)-bicyclo[3.3.0]octan-3-one-2 carboxylic acid steroid esters of formula I

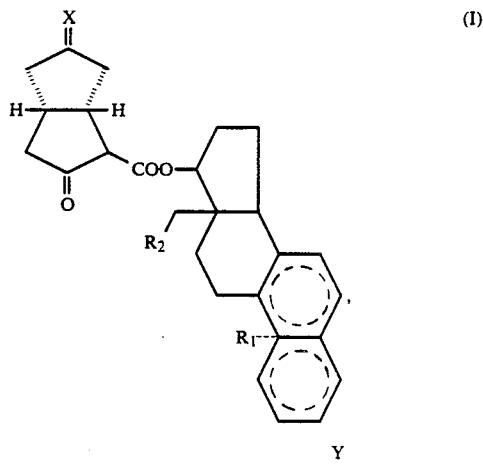

in which
X means oxygen or the radicals —O—(CH$_2$)$_n$—O— or —O—CH$_2$—C(CH$_3$)$_2$—CH$_2$—O—,
n means 2 or 3
R$_2$ means hydrogen or methyl,
Y means the radicals X or X$_1$,
X$_1$ means the radicals OCH$_3$ or OCOR$_3$,
R$_3$ means methyl, ethyl, phenyl, benzyl or pivalyl and the radical

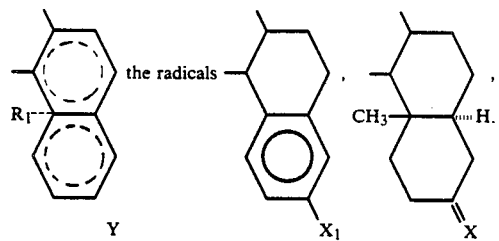

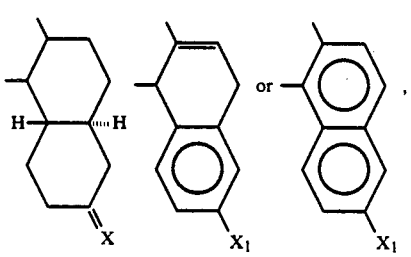

and X and X$_1$ have the meanings indicated above, characterized in that D,L-bicyclo[3.3.0]octan-3-one-2 carboxylic acid esters of formula II

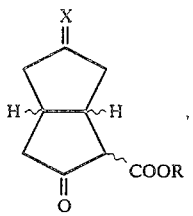

in which

X has the meaning indicated above and R is an alkyl group with 1-4 carbon atoms, with optically active steroids with a free 17beta hydroxy group of formula III

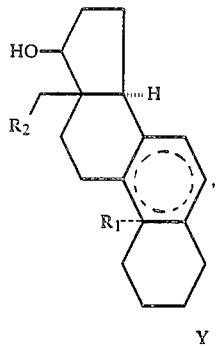

in which $R_2$ and the radical

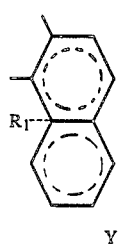

have the meanings indicated above, in the presence of a nucleophilic or acid catalyst is converted into the diastereomeric steroid esters and the optically pure steroid esters of formula I are obtained as crystallizates.

The radicals methyl, ethyl, n-propyl, isopropyl, n-butyl, sec-butyl and tert-butyl are suitable as alkyl groups with 1-4 C atoms.

Estradiol methyl ether as well as compounds of the equilin type or of the equilenin type are suitable as steroids of formula III, which carry a 17beta hydroxy group. As further steroids there can be mentioned those in which gamma=X or $X_1$.

The preferred reactions are explained by the following diagram I: Thus D,L-bicyclo[3.3.0]octane-3,7-dione-2 carboxylic acid methyl ester VI is transesterified with estradiol methyl ether VII in the presence of 4-dimethylaminopyridine (DMAP) or 4-pyrrolidinopyridine (PPY) according to the method of D. F. Taber et al., J.O.C. 50, 3618 (1985) or by acid-catalyzed transesterification in the presence of camphorsulfonic acid acid, p-toluenesulfonic acid or methanesulfonic acid in toluene in about 80-90% yield. In this case, almost optically pure ester VIII crystallizes out in 35-40% yield, while the ester (cf. IV) diastereomeric to VIII remains in solution. With the selective ketalization with neopentyl glycol, VIII yields the steroid ester ketal X. The optically active ketal ester X can also be recovered analogously from D,L-neopentylketal monoethyl ester IX by transesterification with estradiol methyl ether VII in the presence of DMAP or PPY in crystalline form and practically optically pure in about 35-40% yield, and the diastereomer of X remains in the mother liquor.

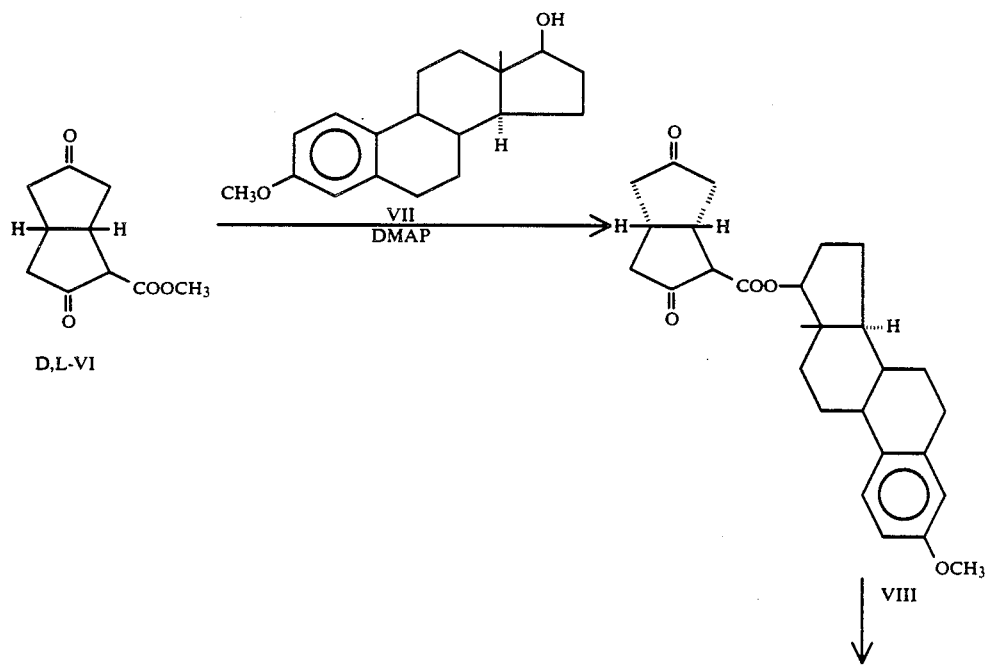
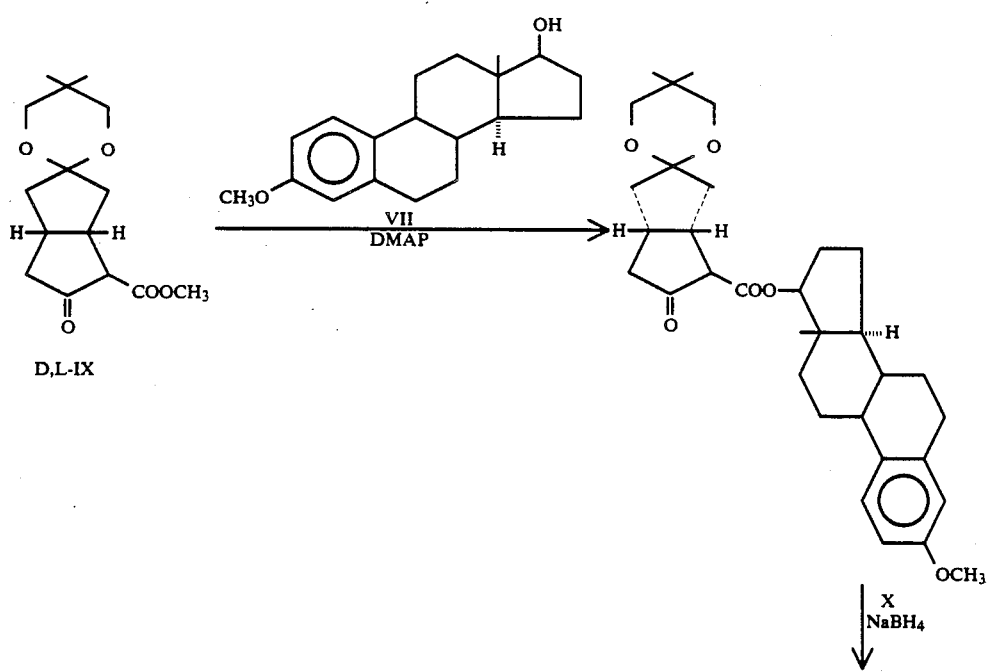

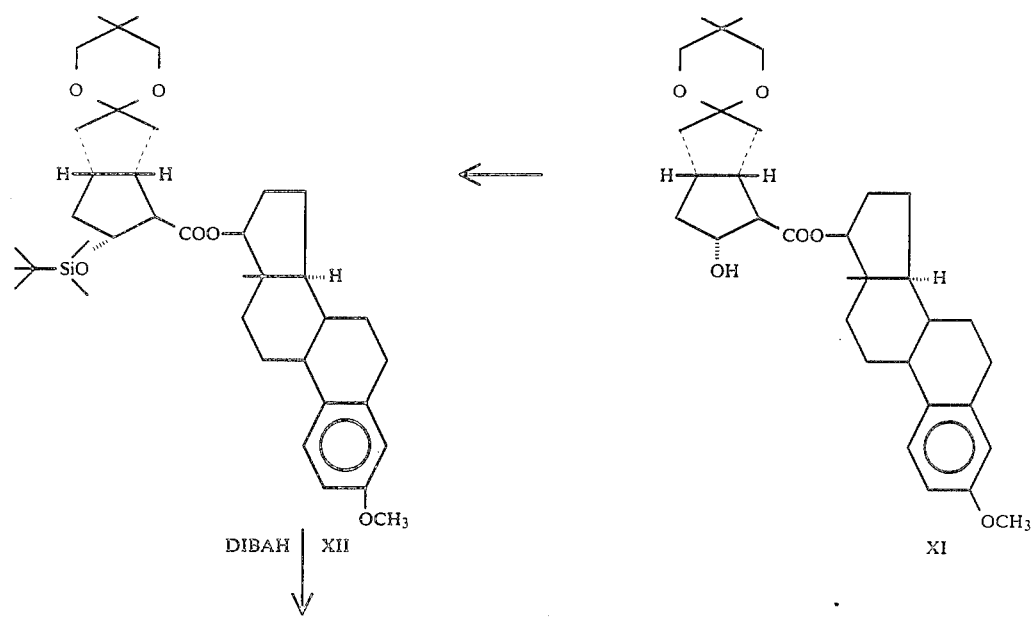
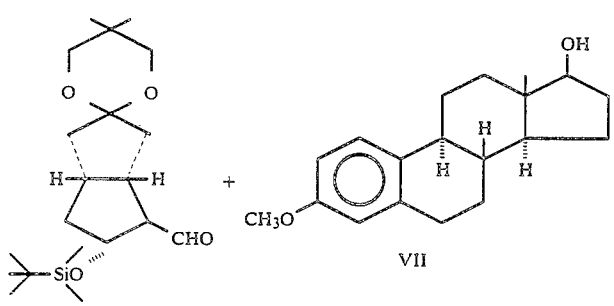
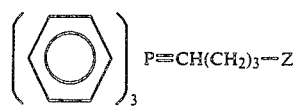
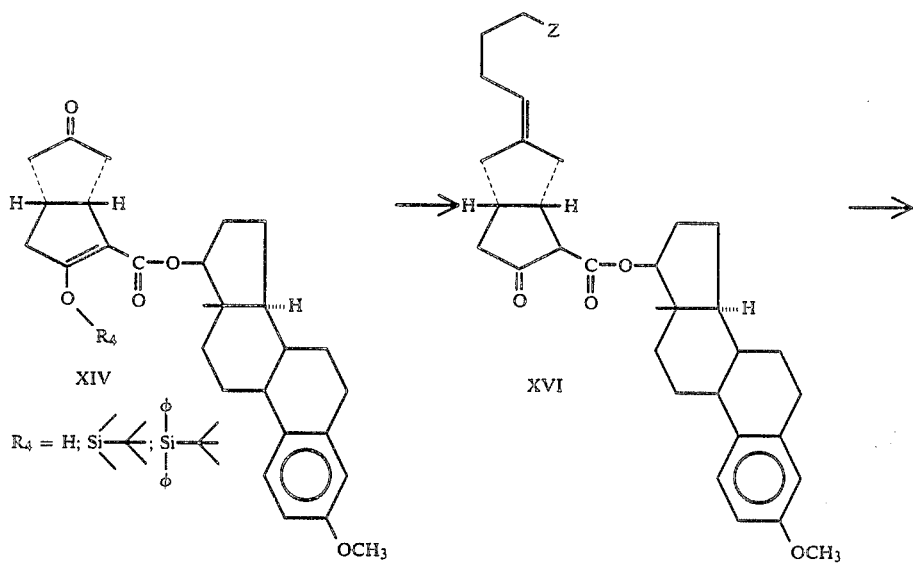

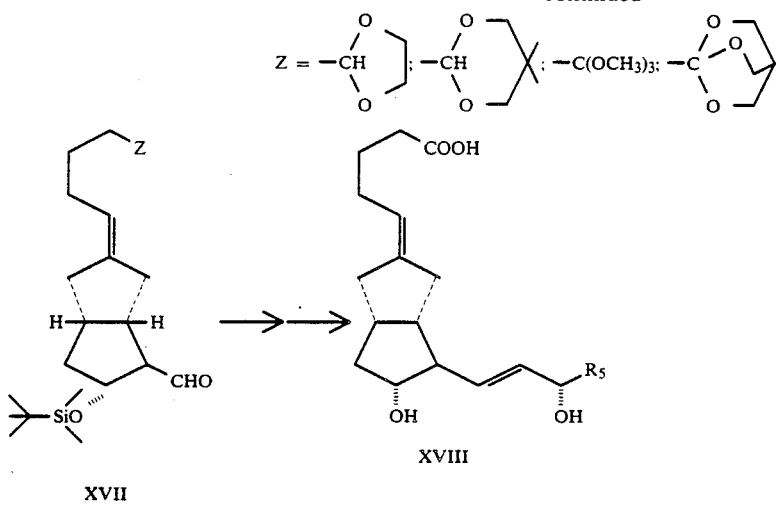

Reduction of X with sodium borohydride in methyl tert-butyl ether H₂O yields the crystalline alcohol XI, whose optical purity of more than 98% can be determined with the help of HPLC on an analytical acid (ODS-Hypersil) with the system acetonitrilemethanol H₂O=33:29:38.

Reduction of the amorphous diastereomeric steroid ester obtained in the evaporation of the mother liquor of X with sodium borohydride in methyl tert-butyl ether H₂O yields the diastereomeric crystalline alcohol of XI, whose optical purity, according to HPLC, is approximately 90%.

Protection of the secondary hydroxyl group of XI with tert-butyl dimethyl silyl chloride yields the crystalline silyl compound XII, which can be reduced at −78° C. with DIBAH to aldehyde XIII and estradiol methyl ether VII. After chromatographic separation, VII can be reused. Aldehyde XIII is reacted in the usual way with Wittig-Horner reagents for introduction of the lower carbacyclin side chain.

With the excess DIBAH the oily 2-hydroxymethyl-3alpha-(dimethyl-tert-butyl-silyloxy)-7-(2,2-dimethyl-1,3-propylenedioxy)-bicyclo[3.3.0]octane is obtained in 70–90% yield.

A further possibility is the direct introduction of the upper side chain in XIV with the help of a 5–6 times excess of Wittig reagents XV to product XVI. The pure 5-E compound XVI, obtained after 5-E/Z separation, can be converted, in an analogous way, to XVII after sodium borohydride reduction, silylation and DIBAH reduction as well as converted to the carbacyclins XVIII after Wittig-Horner reaction, reduction of the 15-keto group and removal of the protecting groups.

In the process for the production of (+)-bicyclo[3.3.-0]octan-3-one-2-carboxylic acid steroid esters of formula I catalytic amounts, i.e., 0.01–0.5 molar amounts, preferably 0.1 mol of a nucleophilic base, e.g., 4-dimethylaminopyridine, 4-pyrrolidinopyridine, 4-piperidinopyridine or polymer-fixed derivatives of these compounds or N-methylimidazole in nonpolar solvents, such as, e.g., dioxane, toluene, xylene, are heated to 80°–160° C., preferably 110°–150° C.

Analogously, I can be produced by heating with 0.01–0.05 molar amounts of sulfonic acids such as camphorsulfonic acid, p-toluenesulfonic acid or methanesulfonic acid in toluene.

The invention also comprises (+)-bicyclo[3.3.0]octan-3-one-2 carboxylic acid steroid esters of formula I as valuable intermediate products for the production of pharmacologically effective carbacyclins of formula XVIII, such as, e.g., Iloprost, which reduces blood pressure and inhibits thrombocyte aggregation or as biologically valuable derivatives of estradiol methyl ether. Further, compounds I or their diastereomers IV are used as valuable intermediate products for the production of natural substances such as sesquiterpenes.

EXAMPLE 1

[(+)-3'-methoxy-1',3',5'-estrarien-17'beta-yl]bicyclo[3.3.0]octane-3,7-dione-2-carboxylate a) 78.48 g (0.4 mol) of D,L-bicyclo[3.3.0]octane-3,7-dione-2 carboxylic acid methyl ester, 114.56 g (0.4 mol) of estradiol-3-methyl ether and 4.89 g (0.04 mol) of 4-dimethylaminopyridine (DMAP) were heated in 1200 ml of toluene in an oil bath of 130° C. and the resulting methanol in mixture with toluene (distillate=220 ml) was distilled off continuously for 4 hours, and the temperature in the flask rose from 105° C. to 111° C.

After cooling, the dark reaction solution was evaporated in a vacuum and the residue dissolved in 500 ml of methylene chloride, filtered over a column produced with methylene chloride with 400 g of iron-free silica gel and rewashed with 3000 ml of methylene chloride and concentrated by evaporation. The partly crystalline residue (about 200 g) was dissolved hot in 350 ml of ethyl acetate and allowed to stand overnight for cooling and crystallization. After filtering and washing with ethyl acetate, 72.1 g (about 40%) of the title compound with a melting point of 159°–165° C. was obtained, $[\alpha]_D=59.5°$ (C=1, CHCl₃).

b) 1.0 g (0.51 mmol) of D,L-bicyclo[3.3.0]octane-3,7-dione-2 carboxylic acid methyl ester VI, 1.46 g (0.51 mmol) of estradiol methyl ether VII and 3.4 mg (0.025 mmol) of anhydrous D,L-camphor-10-sulfonic acid are heated with stirring in 20 ml of toluene for 1 hour in an oil bath of 125° C. with distilling off of a toluene-methanol mixture. The resulting reaction mixture is filtered over a column, produced with a mixture of toluene-ethyl acetate (4:1), of 5 g of iron-free silica gel Merck and rewashed with 50 ml of toluene-ethyl acetate mixture (4:1). The eluate is evaporated and the residue is immediately recrystallized from 5 ml of hot ethyl acetate. A total of 0.828 g (36%) of VII was obtained in two portions $K_1=0.57$ g melting point 169°–171° as well as $K_2=0.258$ g melting point 149°–156°.

EXAMPLE 2

[(+)-3'-Methoxy-1',3',5'-estratrien-17beta-yl]-7-(2,2-dimethyl-1,3-propylenedioxy)-bicyclo[3.3.0]octan-3-one-2-carboxylate a) 50 g (0.177 mol) of (D,L)-7-(2,2-dimethyl-1,3-propylenedioxy)-bicyclo[3.3.0]octan-3-one carboxylic acid methyl ester, 52.98 g (0.186 mol) of estradiol methyl ether and 2.16 g (0.0177) of 4-dimethylaminopyridine (DMAP) were heated in 1000 ml of xylene for 2 hours in an oil bath to 160° C. bath temperature and at the same time about 440 ml of xylene-methanol mixture was distilled off. The remaining solvent amount was distilled off in a vacuum and the 110 g of brownish residue was filtered, after dissolution in 1000 ml of methylene chloride, over a column, prepared from methylene chloride, of 600 g of iron-free silica gel (Merck) and rewashed with 2500 ml of methylene chloride. After evaporation of the filtrate, 90 g of the oily residue was dissolved in 1100 ml of boiling hexane, filtered and allowed to stand to cool. The crystals (32.8 g) with a melting point of 100°–110° C. were filtered off and the filtrate was concentrated by evaporation to 500 ml, and in cooling another 8.49 g with a melting point of 95°–99° C. precipitated. Thus, altogether 41.7 g (43.5%) was obtained. Recrystallization from hexane yielded 32.8 g (34%) of crystals with a melting point of 116°–120° C.

b) 50 g (110.97 mmol) of the compound obtained according to example 1, 12.14 g (116.52 mmol) of 2,2-dimethylpropanediol and 0.734 g (5.55 mmol) of D,L-camphorsulfonic acid as well as 100 g of anhydrous magnesium sulfate, dried at 200° C. in a vacuum, were stirred in 250 ml of dry, alcohol-free methylene chloride for 18 hours at 24° C., filtered and washed with methylene chloride. The yellow oil (68.89 g), obtained after extraction of the filtrate with ice-cold sodium carbonate solution, drying ($Na_2SO_4$) and evaporation, was chromatographed with hexane-ether 8:2 on a column of 340 g of iron-free silica gel. The first 4 l of eluate yielded, after evaporation, 43 g (72%) of crude crystalline title compound, which yielded from 300 ml of hexane the first portion of 27.38 g, melting point 131°–133° C., $[\alpha]_D = +83°$ C. (C=1, $CHCl_3$) and with concentration by evaporation of the mother liquor a second portion of 3.5 g, melting point 128°–130° C. The total yield was 30.88 g = 51.8%. 17.3 g of crude initial material could be recoverd by elution of the column win 1.5 l of methanol and evaporation of the eluate.

EXAMPLE 3

[(+)-3'-methoxy-estratrien-17'beta-yl]-7-(2,2-dimethyl-1,3-propylenedioxy)-bicyclo[3.3.0]octan-3alpha-ol-2-carboxylate 27.1 g (50.5 mmol) of the compound obtained according to example 2 was suspended in 1400 ml of freshly distilled methyl tert-butyl ether and 5.5 ml of $H_2O$ and 4.28 g (126.25 mmol) of sodium borohydride is added with stirring. After 72 hours stirring, 500 ml of $H_2O$ was added and the aqueous phase was extracted several times with methylene chloride. After drying ($Na_2SO_4$) and evaporation, 28.6 g of the crude product was obtained, which crystallized after dissolution in 150 ml of methanol at 0° C. After filtration and washing with ice-cold methanol, 13.16 g of colorless crystals with a melting point of 120°–125° C. was obtained. Concentration of the mother liquor to 60 ml and 40 ml yielded two additional portions of 3.71 g, melting point 99°–105° C., and 0.76, melting point 95°–106° C., i.e., a total of 17.57 g (64.6%). Recrystallization from methanol, yielded the pure title compound of melting point 139°–140° C., $[\alpha]_D = +55.2°$ (C=1, $CHCl_3$).

EXAMPLE 4

[(+)-3'-methoxyestratrien-17'beta-yl]-3alpha-(dimethyl-tert-butyl-silyloxy)-7-(2,2-dimethyl-1,3-propylenedioxy)-bicyclo[3.3.0]octane-2-carboxylate 1 g (1.86 mmol) of the compound obtained according to example 3, 0.47 g (3.06 mmol) of dimethyl-tert-butyl-silyl chloride, 0.25 g (2.04 mmol) of 4-dimethylaminopyridine (DMAP) as well as 0.42 ml (3.06 mmol) of triethylamine were stirred for 18 hours at 24° C., diluted with methylene chloride and the solution was filtered over 3 g of silica gel. After evaporation of the filtrate, the crystalline residue (1.7 g) was extracted with 20 ml of hexane and the solution, after filtration, was evaporated. The residue (1.48 g) was chromatographed on 15 g of silica gel with hexane-ethyl acetate 9:1. The first 200–250 ml of eluate was evaporated and the residue (1.17 g) was crystallized from 10 ml of isopropanol, and 0.72 g of colorless crystals with a melting point of 94°–97° C. $[\alpha]_D + 27.2°$ (C=1, $CHCl_3$) was obtained. Concentration of the mother liquor to 3 ml yielded another 0.15 g of colorless crystals with a melting point of 95°–98° C. The total yield of the title compound was 0.87 g (71.9%).

EXAMPLE 5

2-Formyl-3alpha-(dimethyl-tert-butylsilyloxy)-7-(2,2-dimethyl-1,3-propylenedioxy)-bicyclo[3.3.0]octane A solution of 0.5 g (0.766 mmol) of the compound obtained according to example 4 in 6.5 ml of absolute methylene chloride was instilled in a solution of 1.6 ml (1.915 mmol) of diisobutylaluminum hydride (DIBAH) in toluene at −78° C. within 15 minutes and left for 1 hour at −78° C. After further addition of 1.6 ml (1.915 mmol) of DIBAH solution in toluene it was stirred for another hour at −78° C., then 1.33 ml of isopropanol was carefully instilled and finally 1.33 ml of $H_2O$ and 3.5 ml of methylene chloride were added. After another hour at 78° C., it was allowed to warm to 24° C. and the salts were filtered off, which were carefully rewashed with methylene chloride. After drying ($Na_2SO_4$) and concentration by evaporation, the residue (0.56 g) was chromatographed on a column of 17 g of silica gel with hexane-ethyl acetate 95:5, and 90 g (32%) of pure colorless oily title compound was isolated.

Elution of the $SiO_2$ column with methanol, extraction with hexane, yielded, after crystallization, 170 mg of pure crystalline estradiol methyl ether.

With excess DIBAH there was obtained in 70–90% yield, instead of the title compound, the oily 2-hydroxymethyl-3alpha(dimethyl-tert-butylsilyloxy)-7-(2,2-dimethyl-1,3-propylenedioxy)-bicyclo[3.3.0]octane.

What is claimed is:

1. A process for the production of (+)-bicyclo[3.3.0]octan-3-one-2 carboxylic acid steroid esters of formula I and its diastereomeric steroid ester of formula IV

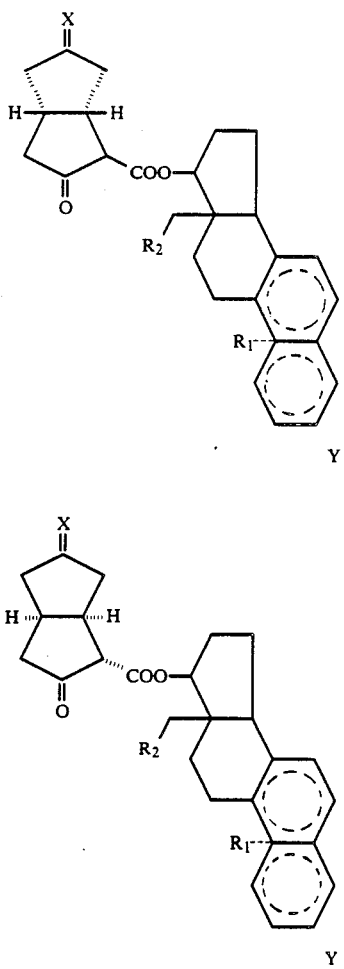
(I)

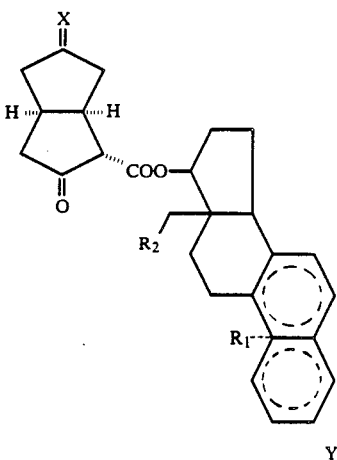
(IV)

in which

X means oxygen or the radicals —O—(CH$_2$)$_n$—O— or —O—CH$_2$—C(CH$_3$)$_2$—CH$_2$—O—, n means 2 or 3

R$_2$ means hydrogen or methyl,

Y means the radicals X or X$_1$,

X$_1$ means the radicals OCH$_3$ or OCOR$_3$,

R$_3$ means methyl, ethyl, phenyl, benzyl or pivalyl, and the radical

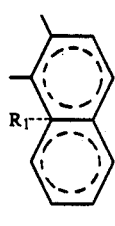 is

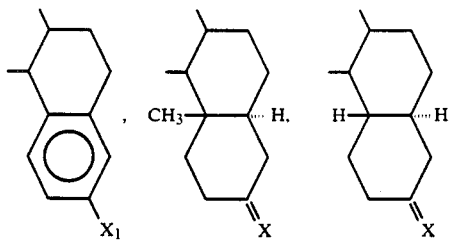

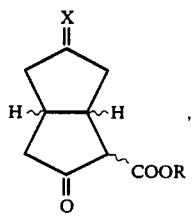

and X and X$_1$ have the meanings indicated above, characterized in that a D,L-bicyclo[3.3.0]octan-3-one-2 carboxylic acid ester of formula II

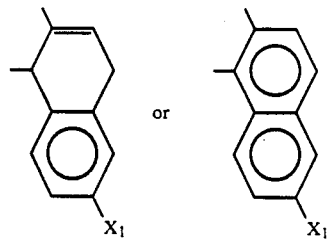
(II)

in which

X has the meaning indicated above and R is an alkyl group with 1–4 carbon atoms, is transesterified with an optically active steroid with a free 17'beta hydroxy group of formula III

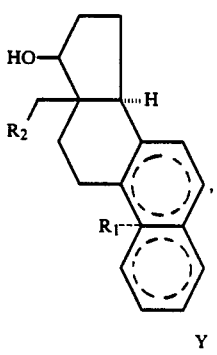
(III)

in which R$_2$ and the radical

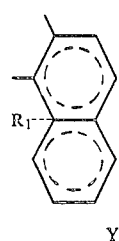

have the meanings indicated above, in the presence of a nucleophilic or acid catalyst, wherein the optically pure steroid esters of formula I can be recovered from the mother liquor in crystalline form.

2. Process according to claim 1, wherein estradiol methyl ether is used as optically active steroid of formula III.

3. Process according to claim 1, wherein there are heated to 80°–160° C. as nucleophilic catalyst 4-dimethylaminopyridine, 4-pyrrolidinopyridine, 4-piperidinopyridine or the polymer-fixed derivatives of these bases or N-methylimidazole or, with the acid catalysts, camphor sulfonic acid, p-toluene sulfonic acid or methanesulfonic acid in nonpolar solvents.

4. (+)-Bicyclo[3.3.0]octan-3-one-2 carboxylic acid steroid ester of formula I

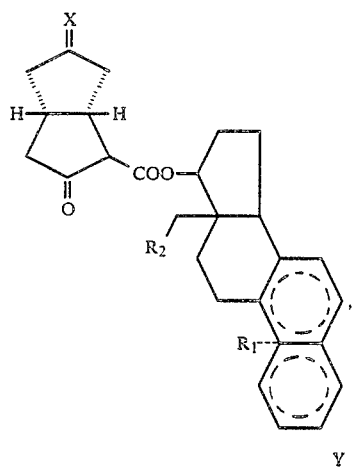

in which
X means oxygen or the radicals —O—(CH$_2$)$_n$—O— or —O—CH$_2$—C(CH$_3$)$_2$—CH$_2$—O—,
n means 2 or 3
R$_2$ means hydrogen or methyl,
Y means the radicals X or X$_1$,
X$_1$ means the radicals OCH$_3$ or OCOR$_3$,
R$_3$ means methyl, ethyl, phenyl, benzyl or pivalyl, and the radical

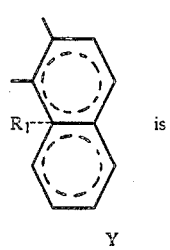

is

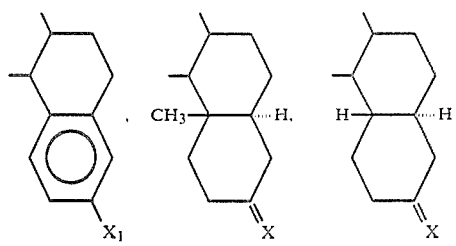

and X and X$_1$ have the meanings indicated above.

5. [(+)-3'-Methoxy-1',3',5'-estratrien-17'beta-yl]-bicyclo[3.3.0]octane-3,7-dione-2-carboxylate, a compound of claim 4.

6. [(+)-3'-Methoxy-1',3',5'-estratrien-17'beta-yl]-7-(2,2-dimethyl-1,3-propylenedioxy)-bicyclo[3.3.0]octan-3-one-2-carboxylate, a compound of claim 4.

7. Bicyclo[3.3.0]octan-3-one-2 carboxylic acid steroid ester of formula IV, in which
X means oxygen or the radicals —O—(CH$_2$)$_n$—O— or —O—CH$_2$—C(CH$_3$)$_2$—CH$_2$—O—,
n means 2 or 3
R$_2$ means hydrogen or methyl,
Y means the radicals X or X$_1$,
X$_1$ means the radicals OCH$_3$ or OCOR$_3$,
R$_3$ means methyl, ethyl, phenyl, benzyl or pivalyl, and the radical

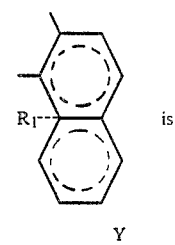

is

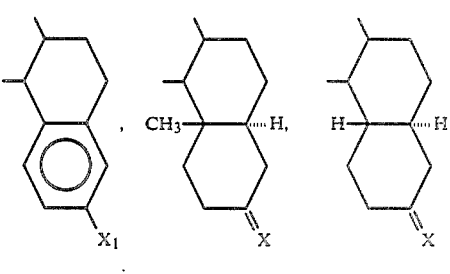

-continued

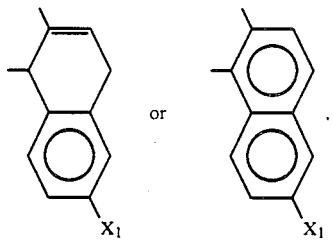

and X and $X_1$ have the meanings indicated above.

8. A process of claim 1, which further comprises converting a (+)-bicyclo[3.3.0]octan-3-one-2 carboxylic acid steroid ester produced by the process of claim 1 into a carbacyclin by reducing the ester group to an aldehyde and reacting the aldehyde with Wittig-Horner reagents to add a lower carbacyclin side chain.

9. A process of claim 8, which further comprises converting a (+)-bicyclo[3.3.0]octan-3-one-2 carboxylic acid steroid ester produced by the process of claim 1 into a carbacyclin by reducing the ketone group of the ester to a secondary hydroxy group, protecting the secondary hydroxy group of the ester with a silyl compound, reducing the ester group to an aldehyde and reacting the aldehyde with Wittig-Horner reagents to add a lower carbacyclin side chain.

10. A process of claim 8, wherein the carbacyclin is Iloprost, a pharmacologically effective carbacyclin.

* * * * *